United States Patent [19]
van der Zel et al.

[11] 4,437,191
[45] Mar. 20, 1984

[54] IMPLANT OF CERAMIC MATERIAL

[75] Inventors: Joseph M. van der Zel, Zwaag; Klaas de Groot, Heemstede, both of Netherlands

[73] Assignee: Delphi Dental Industries B.V., Le Hoorn, Netherlands

[21] Appl. No.: 364,975

[22] Filed: Apr. 2, 1982

[30] Foreign Application Priority Data

Apr. 3, 1981 [NL] Netherlands ................. 8101674

[51] Int. Cl.³ .............................................. A61F 1/00
[52] U.S. Cl. .............................................. 3/1; 3/1.9; 128/92 C; 128/92 G
[58] Field of Search ................. 3/1, 1.9; 128/92 B, 128/92 BC, 92 C, 92 D, 92 G

[56] References Cited

U.S. PATENT DOCUMENTS 3,906,550  9/1975  Rostoker et al. ................ 3/1.912
4,011,602  3/1977  Rybicki et al. ................... 3/1.9

Primary Examiner—Richard J. Apley
Assistant Examiner—D. J. Isabella

[57] ABSTRACT

The invention relates to a new implant material of ceramic material for use in dentistry and medicine for replacing hard tissue, such as dental elements and bones. In order that the material may have sufficient strength characteristics, in particular tensile and bending strength, there is provided a compression element with which the ceramic material, preferably sintered hydroxylapatite, can be brought under compression.

5 Claims, 1 Drawing Figure

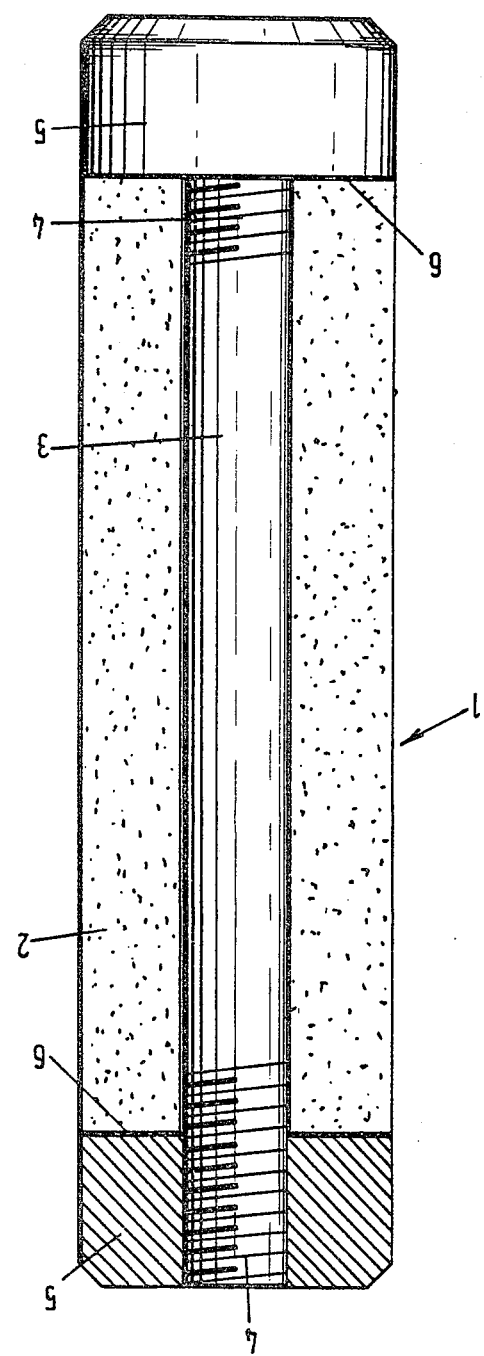

IMPLANT OF CERAMIC MATERIAL

This invention relates to an implant material of ceramic material, e.g. aluminum oxide, sintered tricalcium phosphate material or glass ceramic for replacing hard tissue, for dental and medical uses.

An implant material of this kind is disclosed in U.S. Pat. No. 4,222,128. That patent describes a composite implant material comprising a sintered apatite material, preferably hydroxylapatite, and a thermoplastic or a thermosetting resin. The resin is present in the pores or artificially provided perforations of the apatite material. Thanks to the incorporation of such a resin, a high impact strength can be realized. It does not, however, improve the tensile strength and bending strength.

By ceramic material for the implant is further also understood the so-called "bioglass" (Hench, L. L., Paschall H. A.: Direct Chemical Bonding between bioactive glass ceramic materials and bone. J. Biomed. Mater. Res. 4,25 (1973), or the so-called "Ceravital" (Strunz, V., et al.: Dental Implants using bioactive glass ceramic, 10th Ann. Int. Biomat. Symp., San Antonio 2, 73 (1978). These materials known by the collective name of glass ceramic in essence consist of a glass matrix, in which calcium phosphate is present.

For the bending strength of this kind of material, sometimes a value of 100 N/mm$^2$ is indicated, which however in the case of dynamic load ($2 \times 10^6$ cycles) decreases by a factor 2. Accordingly, it exhibits a great tendency of fatigue fracture.

For some kinds of implants, the bending strength or tensile strength is of little importance, such as for artificial tooth roots (see U.S. Pat. No. 4,222,128, column 4, lines 39–43). For other kinds of implants, such as bone anchorages, artificial teeth, loaded bones, and joints, however, this strength is of great importance. Sintered tricalcium phosphate materials, such as sintered hydroxylapatite, the preparation of which is described, for example, in British Pat. No. 1,522,182, turn out to be inadequate in their bending and tensile strength for such applications.

It is true that, by making the implants of metal (U.S. Pat. No. 3,906,550) or synthetic plastics material (German Auslegeschrift No. 1,042,834) or fibers, such as alumina fibers, glass fibers, carbon fibers, and silicon carbide fibers (German Offenlegungsschrift No. 2,948,792), this drawback can be eliminated, but then this is superseded by many other drawbacks, the most important one of which is poor compatibility with living material, manifesting itself in poor bonding and rejection phenomena. Tricalcium phosphate materials, such as sintered hydroxylapatite do not have this disadvantage: they are non-toxic, non-carcinogenic, and have a good compatibility with living, human or animal tissue.

Implantation tests have shown that under cyclic bending loads, a combination of tensile and bending stresses, hydroxylapatite succumbs to fatigue fracture after a certain time.

Measurements on hydroxylapatite test pieces have shown that its tensile strength is a factor 5 lower than its compressive strength. It is clear, therefore, that in practice hydroxylapatite offers less resistance to tensile forces than to compressive forces. Most materials, including hydroxylapatite, when subjected to fluctuating loading with stresses varied between certain limit values, turn out to fail at an ultimate stress located farther below the static breaking strength, and even below the yield point. This is referred to as fatigue fracture. If the material is subjected to alternating load at a stress below the so-called cyclical stress, fracture does not occur even after an indefinite number of cycles. The cyclical tensile stress of hydroxylapatite is considerably lower than the cyclical compressive stress. If now, from the outside, a constant compressive force is exerted on the hydroxylapatite under cyclical stress loading, the stress will vary around this constant compressive force. If the constant compressive force is selected to be higher than, or equal to the cyclical tensile strength, fracture owing to tensile forces no longer occurs.

It is clear that the constant compressive force must be selected to be lower than half the sum of the cyclical tensile stress and the cyclical compressive stress, and preferably 50 to 75% of this value, because otherwise the risk of cyclical compressive fracture could become too great.

The material according to the present invention is accordingly characterized in that it comprises a compression element, with which the ceramic material can be brought and maintained under compression.

The desired compression can be effected in various ways. In a preferred embodiment, the compression element comprises a rod located centrally within the implant material. This rod can provide the required compression in various ways.

In a preferred embodiment, the rod is at both ends provided with a screw thread with nuts thereon, which can be screwed up over such a distance that the compressive force exerted by the nuts on the ceramic material has the desired value. Preferably, rings of, e.g., platinum or synthetic plastics material are provided between the nuts and the ceramic material for distributing the compressive force exerted over the surface of the implant material.

The implant may be brought under compression immediately after its manufacture. It is also possible, however, that the compression is effected, by simply screwing up one or more nuts, when the implant is introduced. If desired, the nuts are tightened after elongation of the central rod.

In another preferred embodiment, the rod is provided at both ends with solder, which as a result of a melting heat treatment, followed by a solidification cooling treatment, is drawn into contact with the ceramic material owing to the contraction of the rod.

It is also possible for the compression to be realized by the central rod being heated together with the ceramic material, the rod being made of a material having a higher coefficient of thermal expansion than the ceramic material. If thrust bodies are secured to the ends of the central rod, these will generate a compressive force in the ceramic material when the implant is cooled. The same effect can be achieved by cooling after the provision in the center, and possibly at the top and bottom, of a material having a higher thermal contraction, which has been liquified by heating. The compression can also be realized if the central rod has a lower coefficient of thermal expansion than the ceramic material. In that case the rod + ceramic material must first be cooled, whereafter the compressive force contemplated is exerted when the assembly is warmed up.

Further possibilties are the use of a spring for realizing the compression contemplated, and the use of an elongated central wire, for example braided from thinner wires, which after bonding with the ceramic material by means of mechanical retention, by chemical bonding or by an adhesive bond, are capable of exerting a compressive force on the ceramic material.

The compression element can be made in various ways and from various materials. In most cases a metal rod of an alloy having the desired strength and corrosion characteristics will be preferred. Examples are elastic Ni—Cr alloys having a high yield point and tensile strength.

The compression element can also serve as a bone anchoring member.

The invention will be further illustrated with reference to the accompanying drawing, which shows a preferred embodiment of an implant material according to the present invention in cross-sectional view.

Referring to the drawing, there is shown an implant material 1 of sintered tricalcium phosphate material 2, preferably hydroxylapatite, which may contain a certain proportion of whitlockite. Extending centrally through the implant material is a rod 3 of a e.g. Ni—Cr steel, which is provided at both ends with a screw thread 4. Screwed on the ends are nuts 5, which via intermediate rings 6 of, for example, platinum foil, press on the tricalcium phosphate material 2.

EXAMPLE

A concrete example of an implant material according to the drawing comprises a sintered hydroxylapatite cylinder, 12 mm long and having a diameter of 4 mm with a central hole of 1.4 mm. The nuts have a diameter of 4 mm and a length of e.g. 2 mm. The platinum foil is a e.g. 0.03 mm thick. The nuts have been tightened until the hydroxylapatite was brought under a constant compressive force of approximately 8 kg/mm$^2$.

When the bending strength was measured in a 3-point bending test, fracture turned out to occur in the implant under a central load of approx. 30 kg when the nuts were not tightened, and of approx. 40 kg when the nuts were tightened a one-quarter turn (0.30 mm pitch).

Another embodiment could comprise a sintered hydroxylapatite cylinder having a central recess therein in the form of a central hole of 1.4 mm diameter and two disk-shaped recesses having a diameter 0.5 mm less than the outside diameter of the cylinder (4 mm). By pouring into the recess of the pre-heated cylinder an alloy having a higher linear coefficient of thermal expansion than the hydroxylapatite, the hydroxylapatite between the two dishes will be compressed when the assembly is cooled to room temperature. This will increase the bending strength just as in the preceding example.

We claim:

1. A medical implant compatible with bone and similar tissue and exhibiting improved strength when subjected to cyclic bending and tensile stresses comprising a hollow cylindrical ceramic body composed of a material selected from the group consisting of alumina, sintered tricalcium phosphate, and bioactive glass ceramic having a glass matrix containing calcium phosphate, said body being longitudinally compressed by means of a metallic member extending longitudinally through a central portion thereof and by compression means affixed to each end of said metallic member to provide a constant compressive force sufficient to prestress the material of said body wherein the compressive force exterted against said ceramic body is lower than half the sum of cyclical tensile stress and cyclical compressive stress to which the implant will be subjected under normal conditions before implanting the same.

2. An implant according to claim 1, wherein said metallic member comprises a rod extending through the central portion of said body and provided at both ends with screw threads and nuts which upon tightening exert a compressive force on said body.

3. An implant according to claim 2, wherein washers are provided between said nuts and said body to distribute the compressive force over the ends of said body.

4. An implant according to claim 3, wherein said washers are composed of platinum foil.

5. An implant according to claim 1 wherein said metallic member comprises a rod having a higher coefficient of thermal expansion than that of said ceramic body, so that when the implant is assembled in a heated state and then cooled the ceramic body will become compressed by the action of the rod and said compression means affixed to each end of said rod.

* * * * *